(12) United States Patent
Sun et al.

(10) Patent No.: US 10,837,038 B2
(45) Date of Patent: Nov. 17, 2020

(54) ADJUSTING THE PH OF A PRETREATMENT SOLUTION USING CARBON DIOXIDE USEFUL FOR INTEGRATING SACCHARIFICATION AND FERMENTATION

(71) Applicant: National Technology & Engineering Solutions of Sandia, LLC, Albuquerque, NM (US)

(72) Inventors: Jian Sun, Albany, CA (US); Jian Shi, Albany, CA (US); Blake A. Simmons, San Francisco, CA (US); Seema Singh, Mountain House, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/539,614

(22) PCT Filed: Dec. 23, 2015

(86) PCT No.: PCT/US2015/000320
§ 371 (c)(1),
(2) Date: Jun. 23, 2017

(87) PCT Pub. No.: WO2016/105538
PCT Pub. Date: Jun. 30, 2016

(65) Prior Publication Data
US 2017/0369918 A1 Dec. 28, 2017

Related U.S. Application Data
(60) Provisional application No. 62/096,454, filed on Dec. 23, 2014.

(51) Int. Cl.
| C12P 19/14 | (2006.01) |
| C08B 1/00 | (2006.01) |
| C12P 19/02 | (2006.01) |
| C12P 7/10 | (2006.01) |
| C08H 8/00 | (2010.01) |
| C12P 7/64 | (2006.01) |
| C12P 7/06 | (2006.01) |

(52) U.S. Cl.
CPC .............. *C12P 19/14* (2013.01); *C08B 1/003* (2013.01); *C08H 8/00* (2013.01); *C12P 7/065* (2013.01); *C12P 7/10* (2013.01); *C12P 7/649* (2013.01); *C12P 19/02* (2013.01); *C12P 2201/00* (2013.01); *Y02E 50/13* (2013.01); *Y02E 50/16* (2013.01); *Y02E 50/17* (2013.01)

(58) Field of Classification Search
None
See application file for complete search history.

(56) References Cited

FOREIGN PATENT DOCUMENTS

| WO | 2014/172042 A1 | 10/2014 |
| WO | 2014/190294 A1 | 11/2014 |

OTHER PUBLICATIONS

Morais et al. Carbon Dioxide in Biomass Processing: Contributions to the Green Biorefinery Concept, Chemical Reviews, (2015, EPub Nov. 20, 2014), 115: 3-27.*
Al-Mashhadani et al. CO2 Mass Transfer Induced through an Airlift Loop by a Microbubble Cloud Generated by Fluidic Oscillation, Ind. Eng. Chem. Res. 2012, 51, 1864-1877.*
Hou et al. Significantly enhancing enzymatic hydrolysis of rice straw after pretreatment using renewable ionic liquid—water mixtures. Bioresource Technology (2013), 136: 469-474.*
PCT/US2015/00320, "International Search Report and Written Opinion," dated Apr. 8, 2016, 13 pages.
Schubert, "Can biofuels finally take center stage?" *Nature Biotechnology* 24(7) pp. 777-784 (2006).
Gelfand, et al., "Sustainable bioenergy production from marginal lands in the US Midwest," Nature 493 (7433) pp. 514-517 (2013).
Wang, et al., "Ionic liquid processing of cellulose," *Chemical Society Reviews*, 41(4) pp. 1519-1537 (2012).
Shi, et al., Impact of mixed feedstocks and feedstock densification on ionic liquid pretreatment efficiency, *Biofuels*, 41(1) pp. 63-72 (2013).
Li, et al., "Scale-up and evaluation of high solid ionic liquid pretreatment and enzymatic hydrolysis of switchgrass, Scale-up and evaluation of high solid ionic liquid pretreatment and enzymatic hydrolysis of switchgrass," *Biotechnology for Biofuels*, 6 (2013).
Da Silva, et al., "Continuous pretreatment of sugarcane bagasse at high loading in an ionic liquid using a twin-screw extruder" *Green Chemistry* 15(7) pp. 1991-2001 (2013).
Shi, et al., "One-pot ionic liquid pretreatment and saccharification of switchgrass," *Green Chemistry*, 15(9) pp. 2579-2589 (2013).
Ruegg, et al., "An auto-inducible mechanism for ionic liquid resistance in microbial biofuel production," *Nature Communications*, 5 (2014).

(Continued)

*Primary Examiner* — Iqbal H Chowdhury
(74) *Attorney, Agent, or Firm* — Kilpatrick, Townsend & Stockton, LLP (57) ABSTRACT

The present invention provides for a method of fermenting or saccharifying a biomass comprising: (a) (i) contacting a biomass comprising a polysaccharide, and an ionic liquid (IL) to form a first solution, or (ii) providing the first solution comprising the biomass and the IL, (b) contacting the first solution and carbon dioxide such that the first solution results in a lower pH, (c) introducing (i) an enzyme capable of enzymatically to breakdown at least one bond in the polysaccharide or a breakdown product of the polysaccharide, and/or (ii) a microorganism that capable of producing the enzyme and/or fermenting the polysaccharide or a breakdown product of the polysaccharide, such that the polysaccharide is at least partially broken down and the first solution is transformed into a second solution.

17 Claims, 8 Drawing Sheets

(56) References Cited

OTHER PUBLICATIONS

Ninomiya, et al., "Cholinium carboxylate ionic liquids for pretreatment of lignocellulosic materials to enhance subsequent enzymatic saccharification," *Biochemical Engineering Journal*, 71(0) pp. 25-29 (2013).

Ohira, et al., "Design of Cellulose Dissolving Ionic Liquids Inspired by Nature," *ChemSusChem*, 5 pp. 388-391 (2012).

Liu, et al., "Ionic liquids from renewable biomaterials: synthesis, characterization and application in the pretreatment of biomass," *Green Chemistry* 14(2) pp. 304-307 (2012).

Hou, et al., "Evaluation of Toxicity and Biodegradability of Cholinium Amino Acids Ionic Liquids " *PLoS ONE* 8(3):e59145 (2013).

Tome, et al., "Cholinium-based Supported Ionic Liquid Membranes: A Sustainable Route for Carbon Dioxide Separation," *ChemSusChem*, 7(1) pp. 110-113 (2014).

Fukaya, et al., "Bio ionic liquids: room temperature ionic liquids composed wholly of biomaterials," *Green Chemistry*, 9(11) pp. 1155-1157 (2007).

Plechkova, et al., "Applications of ionic liquids in the chemical industry " *Chem. Soc. Rev.*, 37(1) pp. 123-150 (2008).

Petkovic, et al., "Exploring fungal activity in the presence of ionic liquids " *Green Chemistry*, 11(6) pp. 889-894 (2009).

Boethling, et al., "Designing Small Molecules for Biodegradability," *Chem. Rev.*, 107(6) pp. 2207-2227 (2007).

Sun, et al., "Understanding pretreatment efficacy of four cholinium and imidazolium ionic liquids by chemistry and computation," *Green Chem.*, 16(5) pp. 2546-2557 (2014).

Yang, et al., "$CO_2$ capture and activation by superbase/polyethylene glycol and its subsequent conversion," *Energy & Environmental Science*, 4(10) pp. 3971-3976. (2011).

Petkovic, et al., "Ionic liquids: a pathway to environmental acceptability," *Chem. Soc. Rev.*, 40(3) pp. 1383-1403 (2011).

Frederix, et al., "Development of a Native *Escherichia coli* Induction System for Ionic Liquid Tolerance," *PLoS ONE* 9(7):e101115 (2014).

Ober, et al., "pH Control of Ionic Liquids with Carbon Dioxide and Water: 1-Ethyl-3-methylimidazolium Acetate," *Ind. Eng. Chem. Res.*, 51(6) pp. 2524-2530 (2012).

Pera-Titus, "Porous Inorganic Membranes for $CO_2$ Capture: Present and Prospects," *Chem. Rev.* 114(2) pp. 1413-1492 (2013).

Jessop, et al., "Gas-Expanded Liquids " *Chem. Rev.* 107(6) pp. 2666-2694 (2007).

Barber, et al., "Coagulation of Chitin and Cellulose from 1-Ethyl-3-methylimidazolium Acetate Ionic-Liquid Solutions Using Carbon Dioxide," *Angew. Chem. Int. Ed.*, 52(47) pp. 12350-12353 (2013).

Shi, et al., "Understanding the role of water during ionic liquid pretreatment of lignocellulose: co-solvent or anti-solvent?" *Green Chemistry*, 16(8) pp. 3830-3840.

Socha, et al., "Efficient biomass pretreatment using ionic liquids derived from lignin and hemicellulose, " *Proceedings of the National Academy of Sciences*, 111(35): E3587-E3595 (2014).

\* cited by examiner a) Water-wash process    b) JTherm based one-pot process    c) CTec2 based new one-pot process

ADJUSTING THE PH OF A PRETREATMENT SOLUTION USING CARBON DIOXIDE USEFUL FOR INTEGRATING SACCHARIFICATION AND FERMENTATION

RELATED PATENT APPLICATIONS

The present application is a U.S. National Stage Entry of International Patent Application No. PCT/US2015/000320, filed Dec. 23, 2015, which claims priority to U.S. Provisional Patent Application Ser. No. 62/096,454, filed Dec. 23, 2014, which applications are incorporated herein by reference in their entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of pretreatment, saccharification, and fermentation of biomass and related hydrolysates using an ionic liquid conversion technology.

BACKGROUND OF THE INVENTION

Biomass pretreatment using suitable ionic liquids (IL), such as 1-ethyl-3-methylimidazolium acetate, can be highly effective at reducing the recalcitrance of lignocellulosic biomass to enzymatic degradation. However, low biocompatibility of imidazolium based ILs necessitate either extensive water washes or the use of IL tolerant enzyme mixtures, as well as engineered microbial hosts to produce biofuels in the presence of residual ILs present after saccharification. Commercial cellulase mixtures show little or very little activity in the presence of imidazolium based IL. In addition, downstream microbial fermentation show inhibition in the presence of imidazolium based IL and necessitate expression of IL tolerant efflux pumps in the microbial host.

New ILs containing ions derived from naturally occurring bases (such as choline) and acids (such as amino acids) have been developed and tested. The choline based ILs, cholinium lysinate ([Ch][Lys]), show great pretreatment efficiency and also biocompatibility (fuel production in the presence of IL to biofuel producing microbes. However, the activities of commercial cellulase and hemicellulase mixtures are inhibited by the mis-match of operating pHs between pretreatment (using biocompatible cholinium lysinate) and saccharification steps requiring either extensive wash or specialized enzyme mixture for a one-pot, wash free process.

Current methods that carry out pH adjustment (such as using HCl, $H_2SO_4$, $H_3PO_4$, or organic acids, such as formic acid, acetic acid, citric acid, lactic acid and amino acids) create problems such as high salt accumulation, reduced stability of ILs and high cost of separation/recycle of acids and ILs.

SUMMARY OF THE INVENTION

The present invention provides for a method of fermenting or saccharifying a biomass comprising: (a) (i) contacting a biomass comprising a polysaccharide (such as a cellulose, hemicellulose, ligninhemicellulose, lignin, chitin, agarose, or the like, or a mixture thereof), and an ionic liquid (IL) to form a first solution, or (ii) providing the first solution comprising the biomass and the IL, (b) contacting the first solution and carbon dioxide such that the first solution results in a lower pH, (c) introducing (i) an enzyme capable of enzymatically to breakdown at least one bond in the polysaccharide or a breakdown product of the polysaccharide, and/or (ii) a microorganism that capable of producing the enzyme and/or fermenting the polysaccharide or a breakdown product of the polysaccharide, such that the polysaccharide is at least partially broken down and the first solution is transformed into a second solution, (d) optionally separating the solid portion and the liquid portion of the second solution, and (e) optionally recovering the IL from the liquid portion of the second solution.

In some embodiments, the contacting step (a) is a pretreatment of the biomass and the first solution has a temperature ranging from room temperature to about 150° C. Room temperature is a temperature of about 25° C. In some embodiments, during the contacting step (a) the first solution has a temperature ranging from about 100° C. to about 150° C. In some embodiments, during the contacting step (a) the first solution has a temperature ranging from about 100° C. to about 140° C. In some embodiments, the contacting step (b) is a simultaneous saccharification and fermentation and the second solution has a temperature ranging from room temperature to about 37° C.

In some embodiments, the biomass is a biomass derived from a hardwood feedstock, a softwood feedstock, a grass feedstock, or an agricultural waste feedstock, or a mixture thereof. In some embodiments, the biomass comprises switchgrass, sugarcane bagasse, rice straw, corn stover, or a mixture thereof. In some embodiments, the biomass comprises switchgrass, sugarcane bagasse, rice straw, corn stover, or a mixture thereof. In some embodiments, the biomass comprises algal biomass, municipal solid waste, food processing waste, or a mixture thereof.

The suitable ionic liquid (IL) that can be used in the present invention can be any IL capable of deconstructing the biomass. In some embodiments, the IL does not impede the enzymatic activity of the enzyme. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Such suitable IL include, but are limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOSO_3$), 1-ethyl-3-methylimidazolium methylsulfate (EMIM $MeOSO_3$), 1-ethyl-3-methylimidazolium ethylsulfate (EMIM $EtOSO_3$), 1-ethyl-3-methylimidazolium methanesulfonate (EMIM $MeSO_3$), 1-ethyl-3-methylimidazolium tetrachloroaluminate (EMIM $AlCl_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM $HOSO_3$), 1-butyl-3-methylimidazolium methanesulfonate (BMIM $MeSO_3$), 1-butyl-3-methylimidazolium methylsulfate (BMIM $MeOSO_3$), 1-butyl-3-methylimidazolium tetrachloroaluminate (BMIM $AlCl_4$), 1-butyl-3-methylimidazolium thiocyanate (BMIM SCN), 1-ethyl-2,3-dimethylimidazolium ethylsulfate (EDIM $EtOSO_3$), Tris(2-hydroxyethyl)methylammonium methylsulfate (MTEOA $MeOSO_3$), 1-methylimidazolium chloride (MIM Cl), 1-methylimidazolium hydrogensulfate (MIM $HOSO_3$), 1,2,4-trimethylpyrazolium methylsulfate, tributylmethylammonium methylsulfate, choline acetate, choline salicylate, and the like. The ionic liquid can comprises one or a mixture of the compounds. Further ILs are taught in U.S. Pat. No. 6,177,575 (herein incorporated by reference).

In some embodiments, the IL is a biocompatible IL. In some embodiments, the biocompatible IL comprises a naturally occurring anion that does not or does not significantly inhibit growth of the microorganism. In some embodiments, the biocompatible IL is a cholinium based amino acid IL ([Ch][AA] IL) or cholinium based carboxylic acid IL ([Ch][CA] IL), or a mixture of two or more of the cholinium based amino acid and/or carboxylic acid IL. In some embodiments, the amino acid or carboxylic acid is naturally occurring. In some embodiments, the biocompatible IL is biodegradable. In some embodiments, the biocompatible IL is cholinium lysinate, cholinium glutamate, cholinium aspartate, or the like. The biocompatible IL is capable of capturing a high volume of carbon dioxide under ambient or low pressure. The capturing of a high volume of carbon dioxide results in a decreasing of the pH value of the first solution. In some embodiments, the contacting step (b) further comprises introducing an alcohol to the first solution. In some embodiments, the concentration of the biocompatible IL is as high as about 0.25 mM.

In some embodiments, the first solution is either a pure IL or aqueous IL system or an IL/solvent mixture. The pure IL or aqueous IL system or IL/solvent mixture are suitable for use in the biomass pretreatment of the present invention. In some embodiments, the concentration of the IL in its aqueous system is ranged from 0.1-100 wt %. In some embodiments, the concentration of the IL in its aqueous system is ranged from 0.1-50 wt %. In some embodiments, the concentration of the IL in its aqueous system is ranged from 0.1-10 wt %.

In some embodiments, the carbon dioxide is gaseous. In some embodiments, the gaseous carbon dioxide is bubbled through the first solution. In some embodiments, the gaseous carbon dioxide has a pressure of about 1 MPa.

In some embodiments, the enzyme is a cellulase, hemicellulase, or a mixture thereof. In some embodiments, the enzyme is an enzyme derived from a microbial, fungal or bacterial source. In some embodiments, the enzyme is an enzyme that has an optimal activity at a pH from about pH 4.5 to about pH 8.0. In some embodiments, the enzyme is a currently commercially available enzyme, such as CTec2 and/or HTec2.

In some embodiments, the microorganism is a yeast or a prokaryote. In some embodiments, the microorganism is an genetically modified or engineered microbe that produces a fuel or another molecule that the wild-type microbe does not. In some embodiments, the prokaryote is a *Zymomonas, Streptomyces, Clostridium, Klebsiella, Ralstonia, Bacillus, Pseudomonas*, or *Escherichia*. In some embodiments, the *Escherichia* is *Escherichia coli*.

In some embodiments, the separating step (d) comprises centrifuging the second solution.

In some embodiments, the contacting step (a) is repeated with a fresh first solution and the biocompatible IL used comprises in part at least some of the biocompatible IL recovered from the recovering step (e). In some embodiments, the method steps are repeated for a plurality of times wherein for each contacting step (a), except for the first time contacting step (a) takes place, the biocompatible IL used comprises in part at least some of the biocompatible IL recovered from the recovering step (e). In some embodiments, the separating step (d) occurs immediately subsequent to the recovering step (e).

In some embodiments, the method results in glucan, xylan, lignin, or a mixture thereof in the solid portion of the second solution. In some embodiments, the method results in a hexose or oligomer thereof, a pentose or oligomer thereof, ethanol, or a mixture thereof in the liquid portion of the second solution. In some embodiments, the hexose is glucose, fructose, allose, altrose, mannose, gulose, idose, talose, or the like. In some embodiments, the pentose is xylose, ribose, arabinose, xylulose, ribulose, or the like.

The method does not require any wash step, such as one or more wash with water. The method does not require a specialized enzyme cocktail, such as the JTherm enzyme mixture. At no time do the first solution and the second solution comprise an IL that is not a biocompatible IL in a concentration that inhibits growth of the microorganism. A concentration of the IL that is not a biocompatible IL that inhibits growth of the microorganism is 1% or higher, or 5% or higher, or 10% or higher.

In some embodiments, the method further comprises a releasing step comprising releasing the carbon dioxide by either elevating the temperature or introducing nitrogen gas, or both.

In some embodiments, the yield of glucose from the biomass is equal to or more than 85%. In some embodiments, the yield of xylose (monomers, oligomers, or a mixture thereof) from the biomass is equal to or more than 65%. In some embodiments, the yield of glucose from the biomass is equal to or more than 85%, and the yield of xylose (monomers, oligomers, or a mixture thereof) from the biomass is equal to or more than 65%.

In some embodiments, the biomass is a cellulose biomass, hemicellulose biomass, ligno-cellulose biomass, algal biomass, mucipal solid waste, food processing waste, or a mixture thereof.

The method the present invention has one or more of the following advantages: (1) The method enables one-pot IL biomass pretreatment and saccharification processes that do not require special IL tolerant enzyme mixtures, or an extensive wash in traditional two-step IL pretreatment and hydrolysis methods. (2) The method does not require the addition of mineral acids or organic acids to adjust pH. The method relies on the addition of carbon dioxide to adjust pH and avoids the accumulation of salt in the solution. (3) The method enables direct fermentation of sugars from biomass using wild-type fermentation (such yeast or *E. coli* which is not expressing an introduced heterologous efflux pump) host in cholinium and other high pH ILs.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The present invention can be used in the extraction of sugars from biomass. The sugars can be used in all process that use 6-carbon sugars, such as glucose, and the resulting sugars can be used for any intended purpose. The process is of significant interest in biomass processing or biofuels and other biomaterials, paper recycling and pulp processing for paper manufacturing.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Integration of Pretreatment-Saccharification-Fermentation Unit Operations Enabled Via Chemistry Between Ionic Liquid and Carbon Dioxide Pretreatment plays a central role in converting lignocellulosic biomass to fermentable sugars. Many recent progresses urge for a need of feedstock agnostic pretreatment technology and consolidation of unit operations. Ionic liquid (IL) has been demonstrated to be a very efficient and feedstock flexible pretreatment technology and recently shown to have a path forward due to invention of biomass derived renewable IL. However, the integration of IL pretreatment with enzymatic saccharification and fermentation is challenging due to the inhibition of the most effective imidazolium based ILs to commercial cellulase and hemicellulases and also to fuel producing microbes, necessitating extensive water wash, need of IL tolerant enzyme mixture, and IL tolerant fermentation host with expression of an efflux pump. Here we report on overcoming aforementioned limitations by employing several strategies, including use of biocompatible IL and exploiting neat chemistry between IL and carbon dioxide to overcome pH mis-match of operating pHs between pretreatment and saccharification steps and for the first time, demonstration of a one-pot, consolidated pretreatment-saccharification-fermentation process for the production of ethanol from lignocellulosic biomass in IL with commercial mixture and a wild type fermentation host.

1. Introduction

Due to its high abundance and geographic availability, lignocellulosic biomass is a promising feedstock for commercial scale production of fuels and bio-commodities, such as chemicals and bioproducts in a biorefinery concept[1]. However, the efficiently transformation of lignocellulosic biomass is hindered by its recalcitrant nature that retards enzymatic saccharification of biomass to fermentable sugars[2]. To overcome this barrier, several physical and/or chemical pretreatment approaches have been investigated over the past decades.[3] Compared with other popular pretreatment technologies, i.e., dilute acid/base, hot water, and steam explosion pretreatment, ionic liquid (IL) pretreatment has shown some very promising aspects as a pretreatment method. Using certain ILs, such as 1-ethyl-3-methylimidazolium acetate ([C2C1Im][OAc]), a IL pretreatment process can pretreat both single feedstock or a mixture of feedstock, including softwood and hardwood, at high solid loadings[4] and recently has been tested to liters scale,[5] and in continuous mode.[6]

Figure 1:
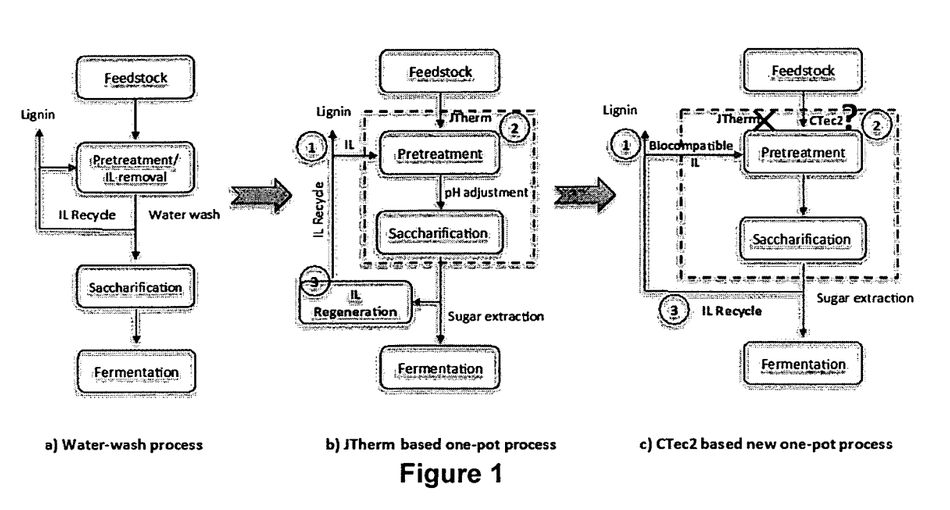
FIG. 1. Strategies to overcome current challenges in one-pot IL pretreatment process: (a) water-wash process; (b) JTherm based one-pot process; and (c) Commercial enzyme and $CO_2$ based new one-pot process.

Despite the high effectiveness of using 1-ethyl-3-methyl-imidazolium acetate ([C2C1Im][OAc]) at reducing the recalcitrance of lignocellulosic biomass to enzymatic degradation, the low biocompatibility of imidazolium based ILs poses strong inhibitory effects to cellulases and fuel fermenting microbes. Thus, the conventional IL pretreatment process often requires extensive water wash to remove IL from pretreated biomass (FIG. 1a). As a result, the associated IL recycling and waste disposal costs create significant economic and process engineering challenges for the commercial scale-up of this technology. To reduce the use of water, a one-pot washing-free process based on [C2C1Im][OAc] was developed recently (FIG. 1b).[7] After treating the switchgrass with [C2C1Im][OAc], the pretreatment slurry was diluted with water to a final IL concentration of 10-20 wt % and directly hydrolyzed using a thermostable IL tolerant enzyme mixture previously, liberating 81.2% glucose and 87.4% xylose (monomers and oligomers).[7] This result provides an instructive concept for developing a more economic IL pretreatment process, however, the JTherm based one-pot process requires specialty enzymes and is not compatible with commercial cellulases/hemicellulose platforms. In addition, downstream microbial fermentation is inhibited by residual imidazolium based ILs thus requiring further separation of sugar from IL stream. Even with the recent discovery and expression/activation of IL efflux pumps in $E.\ coli$[8] greatly improved the tolerance to 6%, constructing of an industrial relevant IL-tolerant fermentation host still need intensive research and development.

To overcome the economical, cytotoxic and environmental concerns of conventional imidazolium ILs, a new generation of ILs containing ions derived from naturally occurring bases (e.g., choline) and acids (e.g., amino acids and carboxylic acids) has recently emerged.[9,10,11,12,13] These ILs contain cholinium cation combined with amino acid-based anions ([Ch][AA] ILs)[11] or carboxylic acid-based anions ([Ch][CA] ILs).[14] Cholinium ILs are intrinsically less expensive (due to the lower cost of cation starting material),[15] more biocompatible,[16] more biodegradable[17] but still high efficiency compared with imidazolium ILs based on our recent study.[18] However, the activities of commercial cellulase and hemicellulase mixtures are still inhibited by the mis-match of operating pHs between pretreatment (utilizing biocompatible cholinium lysinate) and saccharification steps. To enable a one-pot process using biocompatible IL and commercial enzyme mixtures, one must develop a method that overcomes the pH mis-match.

Adjustment of pH using mineral acids, i.e. HCl, $H_2SO_4$, $H_3PO_4$ and/or organic acids, i.e. formic acid, acetic acid, citric acid, lactic acid and amino acids, creates a few problems such as high salt accumulation, reduced stability of ILs and cost of separation/recycle of acids/ILs. Nevertheless, the cholinium based ILs capture high volume of $CO_2$ under ambient or low-pressure[19] leading to pH drop by forming the corresponding carbonate salts. The process is reversible at elevated temperature or when bubbling nitrogen gas like other ILs, which has been reported extensively. In addition, if needed, $CO_2$ absorption efficiency can be further enhanced by introducing a small fraction of alcohol (e.g. ethylene glycol, and polyethylene glycol).[20] Entrenched from this unique property, we developed a novel one-pot pretreatment and saccharification process using biocompatible IL and commercial mixtures (FIG. 1c). Compared with the conventional water-wash process and JTherm based one-pot process, FIG. 1c depicts a new configuration, in which, 1) biocompatible IL, [Ch][Lys] was used instead of [C2C1Im][OAc], 2) special JTherm enzyme mix was replaced by commercial enzyme mixtures for saccharification. In order to provide a balanced pH situation, $CO_2$ is deployed instead of mineral/organic acid for pH adjustment and commercial cellulase and hemicellulases are directly mixed with pretreatment slurry in presence of the biocompatible IL for saccharification. This study opens avenues for developing more environmentally benign and the cost effective processes for sugar production and IL recycling.

Figure 2:
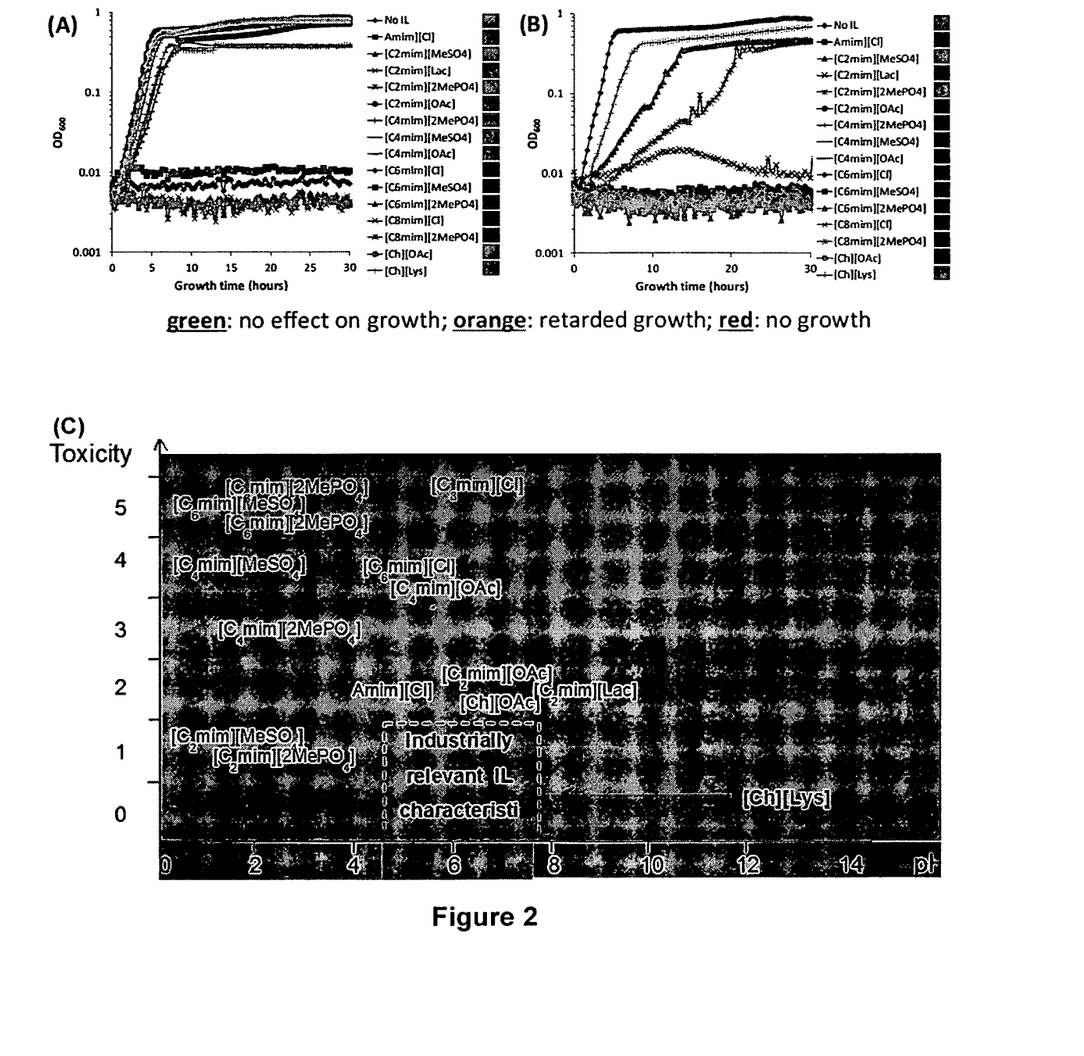
FIG. 2. Toxicity screen of 15 ionic liquids on *Saccharomyces cerevisiae* strain BY4741 at different IL concentrations: (A) 25 mM; (B) 200 mM; and (C) A map of the relationship between pH and toxicity of ILs.

2. Results and Discussions 2.1. Cholinium Based IL is Compatible to Commercial Enzymes and Microbes The new cholinium based IL, cholinium lysinate ([Ch][Lys]) showed great pretreatment efficiency over a range of biomass feedstocks, e.g. sugarcane bagasse, rice straw, switchgrass, etc. Both choline, the cation precursor and lysine, the anion precursor are essential nutrients for microbial growth, which are known to be non-toxic and biodegradable. In this study, we carried out toxicity screen of 15 typical ILs including [Ch][Lys], [Ch][OAc] and imidazolium based ILs, [C2C1Im][OAc] on *Saccharomyces cerevisiae* strain BY4741 at different IL concentrations of 25 and 200 mM (FIG. 2A-2B) in SC medium containing 0.2% glucose with the pH of the IL solution adjusted to 7 using hydrochloric acid if necessary. It aims to test whether the IL, [Ch][Lys] is compatible to commercial enzymes and biofuel producing microbes. As shown in FIG. 2A-2D, the microbial growth was completely jeopardized in a concentration of 200 mM (~4.3 wt %) for most of the ILs. However, no retard of microbial growth was observed in media at [Ch][Lys] concentrations of 200 mM (~5 wt %) of [Ch][Lys]. Results indicate that [Ch][Lys] is intrinsically less toxic to *S. cerevisiae*.

Figure 6:
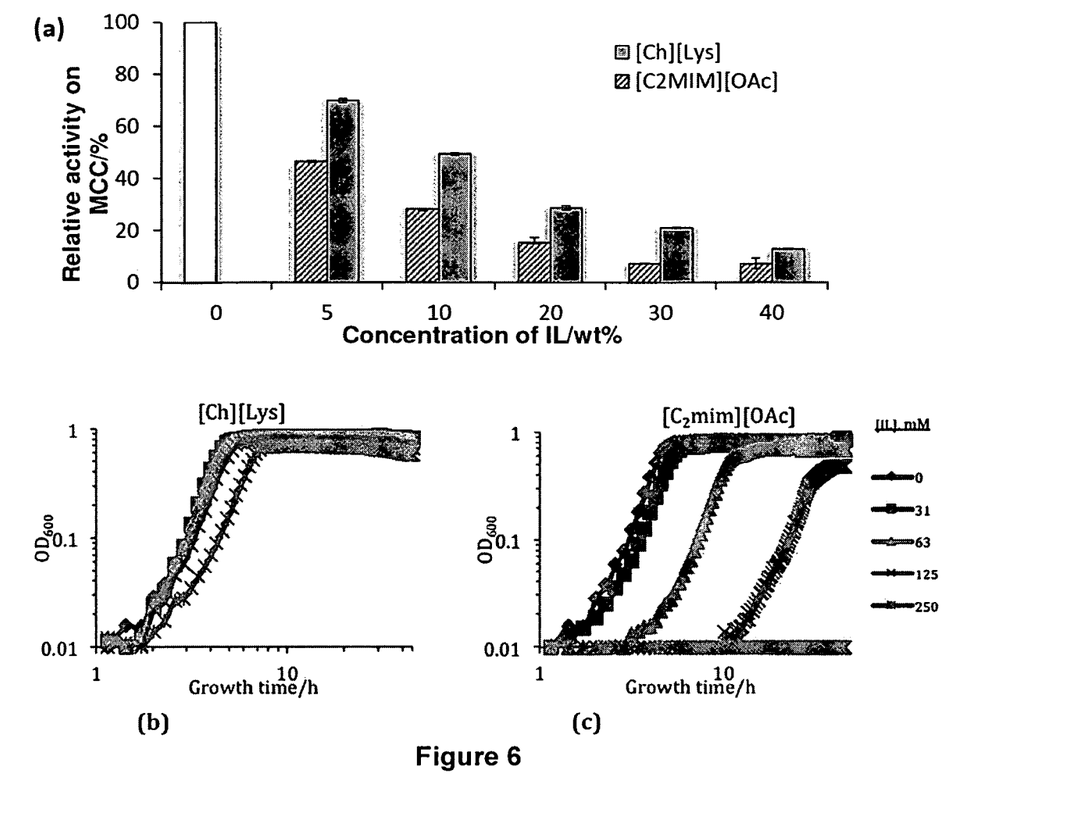
FIG. 6: Inhibition of ILs to (a) the hydrolysis of Avicel by commercial enzyme mixtures, and (b) and (c) microbial growth of *E. coli*.

We also compared [Ch][Lys] with [C2C1Im][OAc] on their compatibility with commercial enzyme mixtures, i.e., CTec2+HTec2 (9:1, v/v) with the pH of the IL solution adjusted to 4.5 using hydrochloric acid (FIG. 6a). When exposed to various concentrations of [C2C1Im][OAc] (40, 30, 20, 10, 5 and 0 wt %), the relative activities of enzymes (in term of sugar yield from enzymatic hydrolysis of microcrystalline cellulose) decrease rapidly. With 5% [C2C1Im][OAc], the relative activity is only 47% of the no-IL control; while only 30% activity remains at 10% [C2C1Im][OAc]. However, [Ch][Lys] shows much less inhibition to enzyme activities, with almost 70% and 50% of its original activity remain at 5% and 10% [Ch][Lys], respectively.

Results indicate that [Ch][Lys] is intrinsically less toxic to microbes.[21] With the new discovery of an efflux pump and its regulator encoded by eilA from *Enterobacter lignolyti*- cus, researchers were able to construct an *E. coli* strain tolerant to 6% [C2C1Im][Cl] by the heterologous expression of the IL efflux pump.[8, 22] However, further strain development is needed to improve the stability and fuel production. Based on the result above, a map with the relationship between pH and toxicity of the 15 ILs was illustrated in FIG. 2C. To enable an industrially relevant IL pretreatment process, the IL needs to have lower microbial and enzymatic toxicity, high pretreatment effectiveness and a mild pH range ~4.5-7.5. Clearly, [Ch][Lys] owns some very desirable characteristics; however, the pH range is not matching that for enzymatic saccharification and microbial fermentation.

2.2. pH Adjustment Using Mineral/Organic Acids is Problematic

Figure 7:
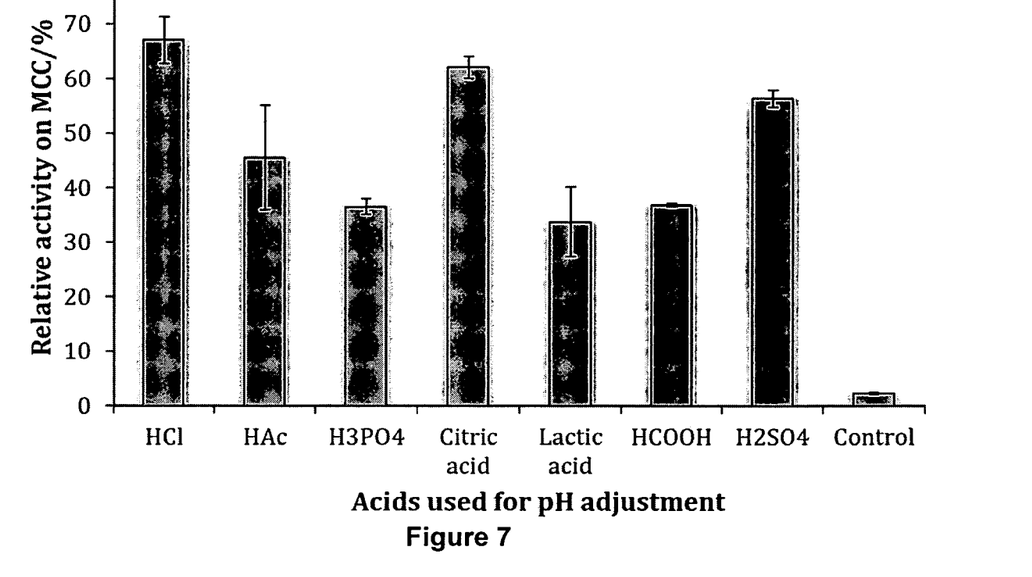
FIG. 7: Effect of acids-induced pH adjustments on enzymatic hydrolysis of MCC.

Knowing that [Ch][Lys] is more compatible to commercial enzymes and fuel-producing microbe, the [Ch][Lys] or its aqueous [Ch][Lys] solution are very basic during and after pretreatment, with pH ranging from 12-14. To enable a one-pot process, the pH mis-match must be adjusted to lower the pH of pretreatment slurry to a range suitable to enzymes and microbes. We tested a series of mineral and organic acids such as hydrochloric acid, phosphoric acid, sulfuric acid, acetic acid, citric acid, lactic acid, formic acid for the pH adjustment of 5% [Ch][Lys] solution. FIG. 7 shows the relative activities of enzymes (in term of sugar yield from enzymatic hydrolysis of microcrystalline cellulose) as a function of the acids used for pH adjustment. Clearly, without pH adjustment, the enzyme activity is very low due to the deactivation/denaturing of enzyme protein under very high pH. Although, enzyme activities could be partially rescued after pH adjustment, low relative activities (<50%) on MCC were observed on those using acetic acid, lactic acid, formic acid, and phosphoric acid for pH adjustment, probably due to toxicity of these anions or high ion strengths due to salt formation. Using hydrochloric acid, citric acid and sulfuric acid for pH adjustment outperforms the other acids, however, because of the nonvolatile nature of both the IL and the acid/salts, separation and recovery of the salts are very challenging. Furthermore, introducing strong acids can be deleterious to [Ch][Lys] due to the replacement of lysinate with other anions.

2.3 Reversible $CO_2$-Based pH Adjustment

Figure 3:
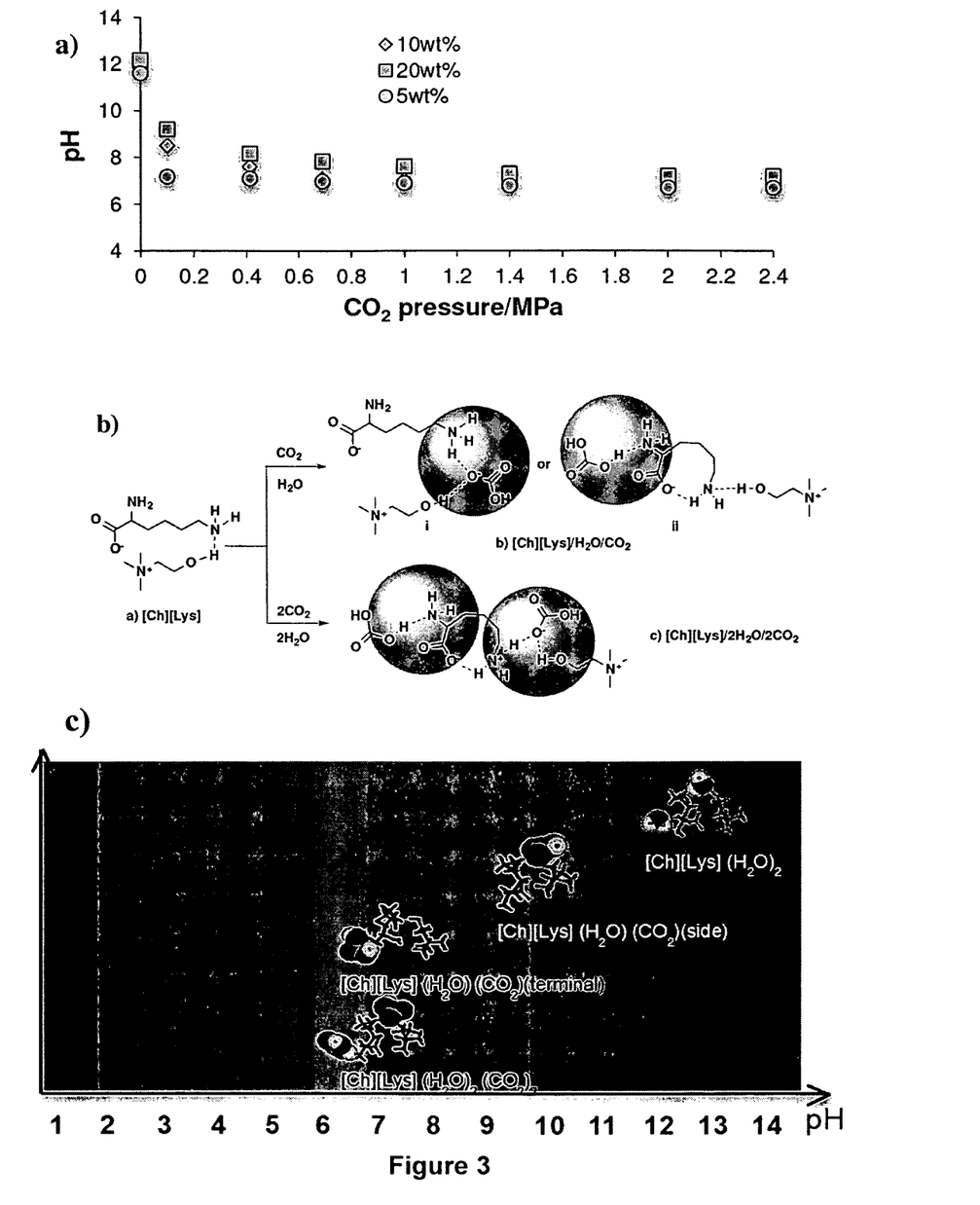
FIG. 3. [Ch][Lys]/$CO_2$ based saccharification process. (a) Effect of $CO_2$ pressure on the pH value of [Ch][Lys]/$H_2O$ systems under the conditions of 10 wt % IL, 20° C. and 1 h; (b) Schematic of reversible $CO_2$-induced pH shifting for [Ch][Lys]; (c) Molecular structure and calculated acidity of [Ch][Lys]/$CO_2$/water system.

The problems of using mineral/organic acids for pH adjustment favor the use of a volatile acidification agent, such as $CO_2$.[23] As a basic IL, [Ch][Lys] is high effective on capturing $CO_2$, compared with many imidazolium based ILs.[24, 25] FIG. 3a shows the pH drop as a function of $CO_2$ pressure (0-2.4 MPa) for three different [Ch][Lys] concentrations (5, 10 and 20 wt %) in water at room temperature. With the increasing of $CO_2$ pressure from 0 to 0.1 MPa, pH values of all [Ch][Lys]-water solutions decrease sharply from pH of ~12 to pH of 7-9. Further increasing $CO_2$ pressure led to further pH drop. For 20 wt % [Ch][Lys]-water solution, a pH value of 7.2 was obtained at a $CO_2$ pressure of around 2 MPa. However, only 0.7 MPa $CO_2$ pressure is needed to drop the pH of 10 wt % [Ch][Lys]-water solution to 7.1. While, only 0.1 MPa $CO_2$ pressure is needed to low the pH of the 5 wt % [Ch][Lys]-water solution to around 6.9, similar to or lower than the typical pressure deployed for carbonating a can of Soda. The process is reversible by increasing temperature or bubbling $N_2$, driving out the $CO_2$ and restoring the pH to its original value. In addition, a small fraction of alcohol (e.g. ethylene glycol) could be introduced for further enhancing $CO_2$ absorption efficiency if necessary.[20]

Figure 8:
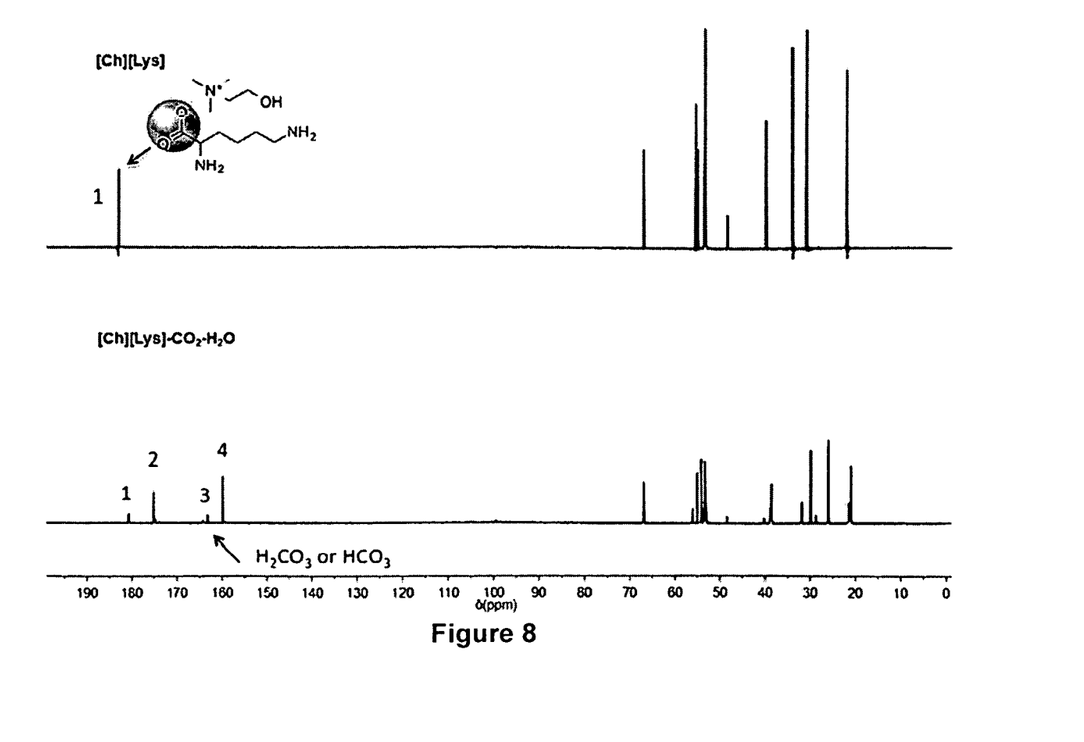
FIG. 8: $^{13}C$ nuclear magnetic resonance (NMR) analysis of [Ch][Lys] before and after $CO_2$ absorption.
Figure 9:
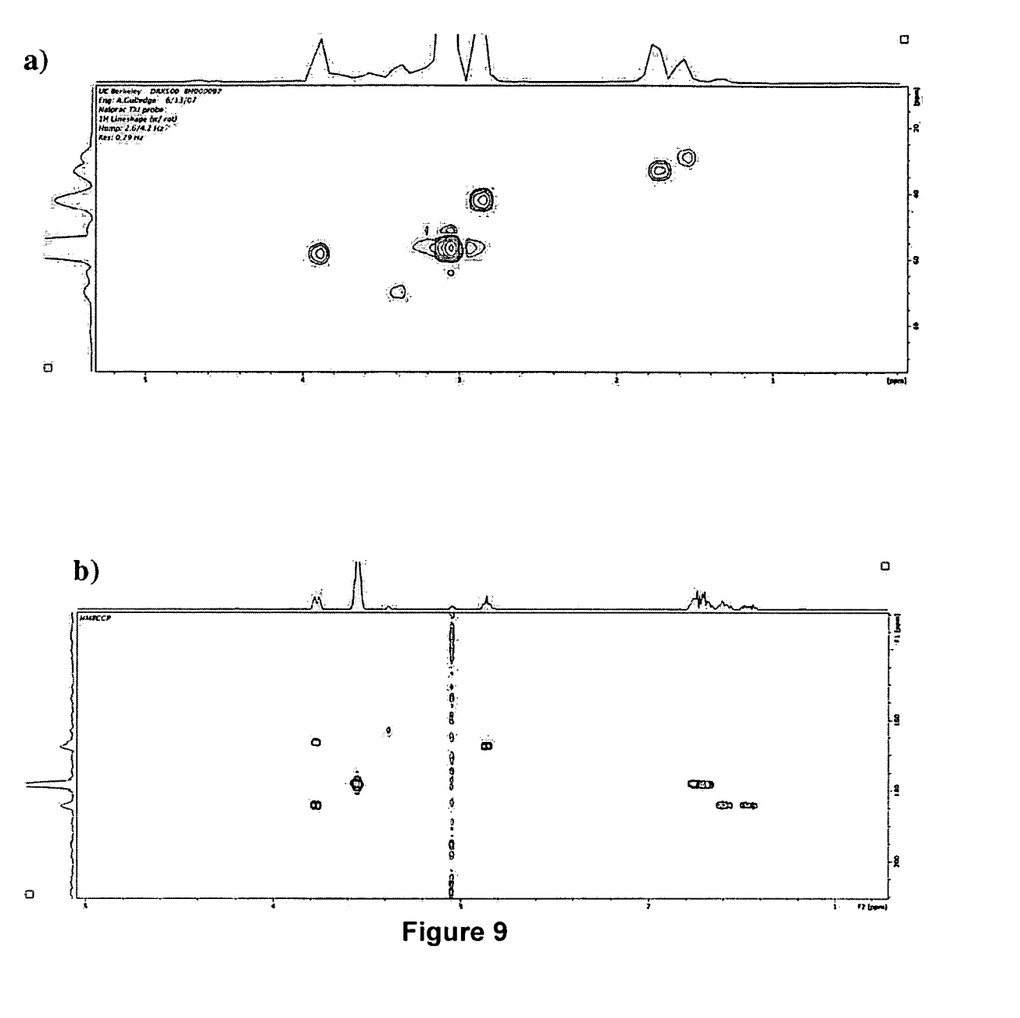
FIG. 9: Two-dimensional (2D) $^{13}C$-$^1H$ heteronuclear single quantum coherence (HSQC) nuclear magnetic resonance (NMR) analysis of [Ch][Lys] before and after $CO_2$ absorption.

Chemistry of aqueous [Ch][Lys] interaction with $CO_2$ is systematically investigated using hybrid Density Functional Theory (DFT) based quantum chemistry approaches and nuclear magnetic resonance (NMR) analysis (FIGS. 8-9). Interactions with $CO_2$ with amine containing molecule were under go either carbamate or carbamic acid reactions pathways. In the presence of water, $CO_2$ reaction mechanism proceeds via bicarbonate pathway. One or two moles of $CO_2$ can bind to the amine groups in lysinate anion and $CO_2$ can further dissolves in the presence of water, forming carbonic acid and in turn lowering the pH (FIG. 3b). The solubility of $CO_2$ increases by increasing the partial pressure of $CO_2$. Higher basicity of [Ch][Lys] is mainly due to the unprotonated side chain amine group (FIG. 3b, red). Protonating the amine can reduce the basic nature of this group and overall reduction of pH. As an individual [Ch][Lys] IL, side chain amine group of [Lys] anion is forming hydrogen bonding with hydroxyl group of its counterpart [Ch] cation (FIG. 3b). We have also calculated acidity of these complexes and the local nucleophilicity index of nitrogen atom and the results are summarized in Table 1. Our calculation results demonstrate that terminal amine group plays a crucial role in pH reduction.

TABLE 1

Calculated acidity of [CH] [Lys] IL with $CO_2$ and water molecules and local chemical reactivity descriptors of terminal and side chain N atoms.

| | Calculated Acidity (eV) | $f_k^-$ Terminal | $f_k^-$ Side |
|---|---|---|---|
| [Ch][Lys] $(H_2O)_2$ | 2.3 | 0.142 | 0.039 |
| [Ch][Lys] $(H_2O)$ $(CO_2)$ (side) | 2.36 | 0.291 | 0.007 |
| [Ch][Lys] $(H_2O)$ $(CO_2)$ (ter.) | 2.7 | 0.015 | 0.065 |
| Ch][Lys] $(H_2O)_2$ $(CO_2)_2$ | 2.7 | 0.017 | 0.026 |

Figure 10:
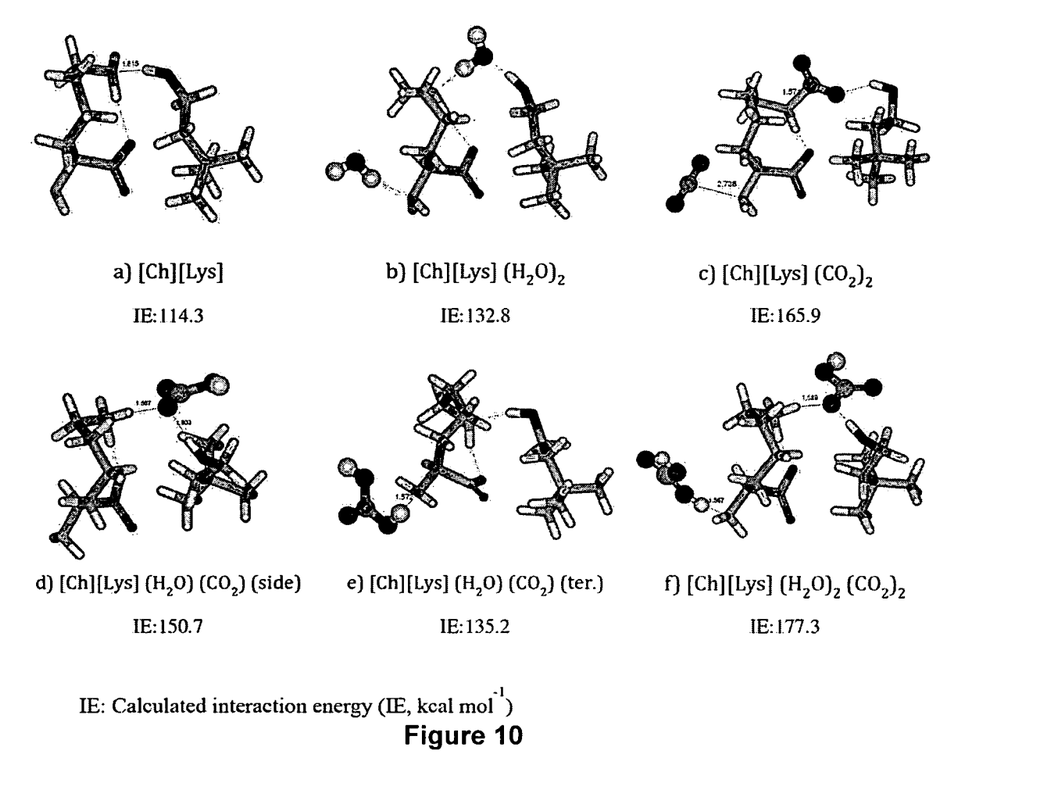
FIG. 10: Calculated interaction energy (1E in kcal mol$^{-1}$) profiles and optimized structures (in Å) of species for [Ch][Lys] via the $CO_2$ mediated pH shifts in the presence of $H_2O$. IE: calculated interaction energy (1E, kcal mol$^{-1}$).

Also as shown in FIG. 3b, interactions between water and side chain amine form a cyclic hydrogen-bonding network to bridge cation and anion. This side amine chain group interacts strongly with $CO_2$ than with the terminal amine group (FIG. 3b, blue sphere). Optimized structure indicates that side chain amine becomes a protonated amine when interacting with $CO_2$ in the presence of water. The corresponding interactions were verified by the multiple peaks with the range of 160-185 ppm in $^{13}$C-NMR spectrum (FIG. 8). Calculated acidity values of these IL-water-$CO_2$ complexes show a clear trend that $CO_2$ interactions with aqueous [Ch][Lys] increase the acidity and thereby decrease the pH (FIG. 10). Interestingly both [Ch][Lys] $(H_2O)_2$ $(CO_2)_2$ complex (FIG. 3a) and one $CO_2$ interacting with [Ch][Lys] $(H_2O)$ forming a bicarbonate IL complex, [Ch][Lys] $(H_2O)$ $(CO_2)$ complex (terminal) (FIG. 3a, ii) having same acidity values. To confirm this observation, we calculated the local chemical reactivity descriptor for nucleophilic attack ($f_k^-$) of the nitrogen atom in terminal and side chain groups (FIG. 3c and FIG. 10). Conceivably, computed $f_k^-$ values are in good agreement with the increasing acidity trend observed using global reactivity descriptors. It is worth to point out that side chain amine group as a bare IL and a complex interacting with water is reducing its basicity on the other hand terminal amine group is not affected. Due to the local charge distribution impacting the basicity and the terminal amine group driving the molecular control of changing the pH with $CO_2$ interactions. Saturating amine group influence on reducing the pH of [Ch][Lys], particularly terminal amine group act as a chemical trigger.

2.4 One-Pot Pretreatment and Saccharification Using Biocompatible IL and $CO_2$ The reversible feature of $CO_2$—[Ch][Lys]-water complex provides an unique opportunity for using $CO_2$ as a cheap, non-toxic and volatile agent to adjust the pH thus enables a new one-pot pretreatment and saccharification process using biocompatible IL and $CO_2$. Compared with the conventional water-wash process and JTherm based one-pot process, the present work depicts a new configuration, in which, 1) biocompatible IL, [Ch][Lys] was used instead of [C2C1Im][OAc], 2) special JTherm enzyme mix was replaced by commercial enzyme mixtures for saccharification; 3) $CO_2$ was used for the reversible pH adjustment followed by simple lignin separation and recycling of IL. $CO_2$-based pH adjustment eliminates the addition of mineral acids and salt accumulation; thus greatly facilitates downstream salt removal and IL recycling. Moreover, the use of $CO_2$ allows separation of acid-insoluble lignin as being demonstrated in a Kraft pulping process.[26]

Figure 4:
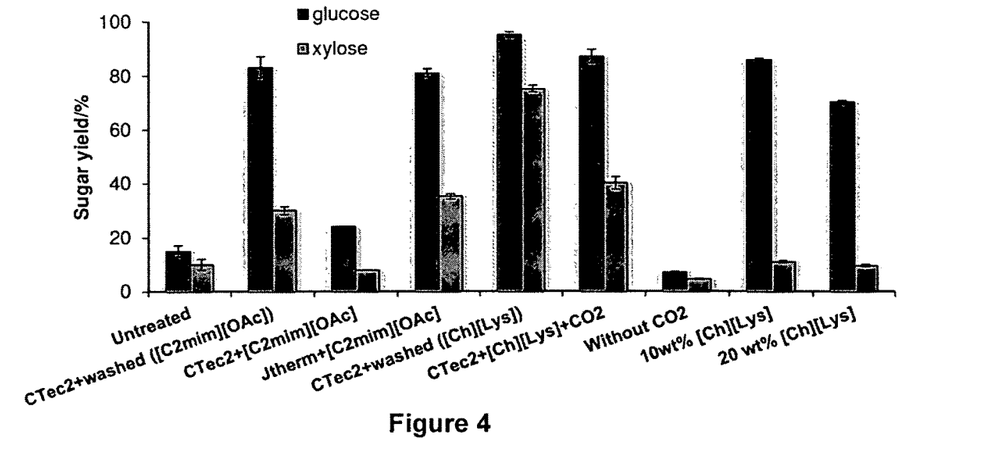
FIG. 4. Sugar yield obtained with different conditions. Conditions: a) [C2C1Im][OAc]: pretreatment, 10 wt % SG loading, 90 wt % IL, 160° C. for 3 h; saccharification, dilute to 10 wt % IL, 5.75 mg JTherm mix/g raw SG, 70° C. for 72 h; b) [Ch][Lys]: pretreatment, 10 wt % SG loading, 90 wt % IL, 140° C., 1 h; saccharification, dilute to 10 wt % IL, 10 mg CeTec mix/g raw SG, 50° C., 1 MPa for 72 h; c) dilute [Ch][Lys]: pretreatment, 1 or 2 wt % SG loading, 10 or 20 wt % IL, 140° C., 1 h; saccharification, no dilute, 10 mg CTec2+HTec2 mix/g raw SG, 50° C., 1 MPa for 72 h.

A side-by-side comparison of the aforementioned three processes was illustrated in FIG. 4, showing the glucose and xylose yields liberated from switchgrass during pretreatment and saccharification. $CO_2$ and [Ch][Lys] based one-pot process achieved 87% glucose and 40% of xylose yield after 72 h saccharification, which is comparable to that of the conventional water-wash process and higher than the JTherm based one-pot process. It is also noticed that sugar yield from $CO_2$ and [Ch][Lys] based one-pot process was also higher than that obtained by using HCl pH adjustment (FIG. 7).

In order to reduce process complexity and improve overall process economics, using aqueous IL in water as pretreatment medium is more favored over the use of anhydrous IL.[27] Recent studies have demonstrated that lower IL concentrations (10-50 wt %) in water may also be effective in pretreating biomass[27]. FIG. 4 also compares sugar yields from one-pot processing started with pretreatment by different [Ch][Lys]-water solutions. It is shown that 85% glucose yield and 11% xylose yield (monomer) was achieved using 10 wt % [Ch][Lys]-water as pretreatment medium and throughout the saccharification steps, whose glucose yield is comparable with that from pretreatment using 100 wt % IL and subsequent dilution to 10 wt % IL for saccharification. Results clearly demonstrate the feasibility of using aqueous [Ch][Lys] solution throughout the one-pot process. Using IL-water mixture as pretreatment agent and throughout the whole process offer a few advantages such as lower viscosity, lower energy inputs and costs, and elimination of the dilution of pretreatment slurry for saccharification and dehydration of saccharification hydrolyzate for IL recycle.

2.5 Simultaneous Saccharifcation and Fermentation and Mass Balance

Figure 5:
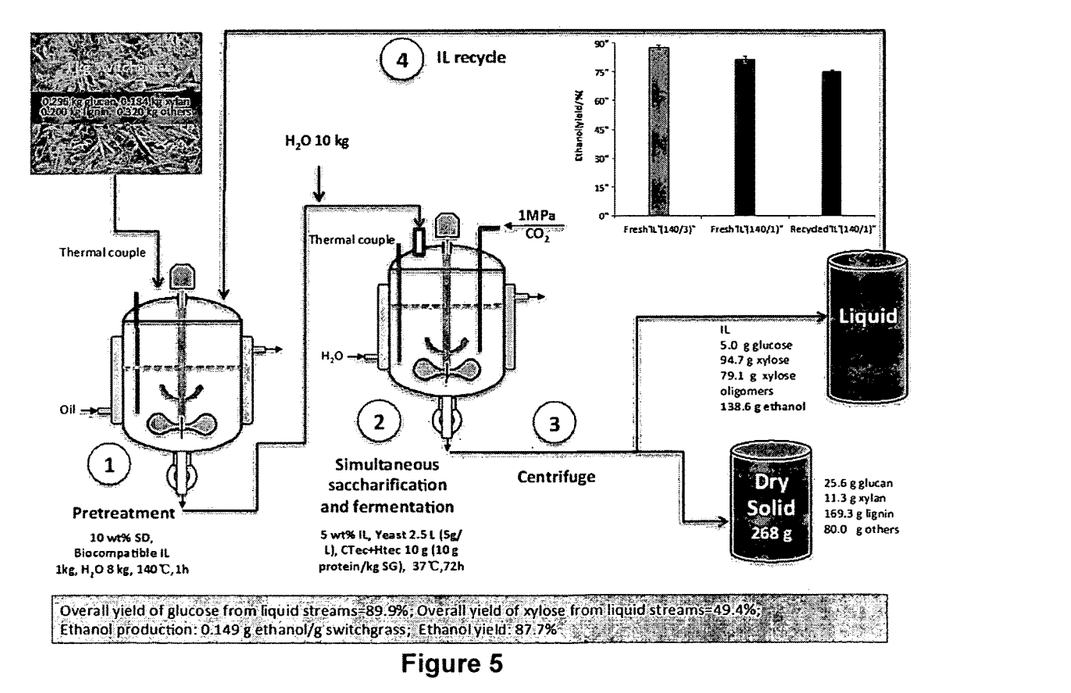
FIG. 5: Ionic liquid recycle result and overall mass balance of the one-pot consolidated processing of switchgrass using [Ch][Lys] and carbon dioxide. Conditions: Pretreatment, 10% SG loading, 140° C., 1 h; Saccharification, 10 wt % IL, 10 mg EP/g SG, 50° C., 18 h and 1 MPa; Simultaneous saccharification and fermentation, 5 wt % IL, 5 g/L yeast cells (based on dry weight), 37° C., 72 h. The overall yield of glucose from the liquid streams is 89.9%. The overall yield of xylose from the liquid streams is 49.4%. The ethanol production is 0.149 g ethanol/g switchgrass. The ethanol yield is 87.7%

We further extended the scope by conducting simultaneous saccharification and fermentation to produce ethanol using wild type yeast in conjunction with the previous developed one-pot pretreatment and saccharification. The mass flows of glucan, xylan, lignin and ethanol were tracked down in each of the streams coming in and out from the one-pot consolidated processing of switchgrass using [Ch][Lys] and $CO_2$. FIG. 5 depicts ethanol productivity of 0.149 g ethanol/g starting switchgrass, which translates to 87.7% of the theoretical ethanol yield from available glucan in starting biomass. It is also noted that only ~10% of the glucan and 16% the xylan was intact in residual solids confirming that most of the sugars have been released/utilized during pretreatment and SSF. The majority of the lignin (~85%) was recovered in the residual solid streams with the molecular weight distribution in a lower range than the native lignin in raw switchgrass suggesting that the lignin polymers were depolymerized during IL pretreatment. After fermentation, the produced ethanol and IL in the liquid stream can be easily separated and recovered by azeotropic distillation. The effectiveness of recycled IL was retained compared with neat IL as indicated by the nearly identical sugar yield after pretreatment and saccharification (FIG. 5). The results provided a successful example of consolidated bioprocessing with an additional advantage of facilitated IL recycle and lignin recovery.

3. Conclusions

We have demonstrated a strategy to overcome the current challenges in one-pot ionic liquid pretreatment and saccharification by using biocompatible IL [Ch][Lys] and $CO_2$. Compared with [C2C1Im][OAc] the imidazolium based IL, [Ch][Lys] is more benign to commercial enzyme mixtures and *E. coli* while still provides equally high pretreatment effectiveness. A new reversible $CO_2$-based process was deployed to replace mineral/organic acid pH adjustment. The use of $CO_2$ in combination of biocompatible IL represents a novel one-pot process that: 1) enables consolidated IL biomass pretreatment and saccharification/fermentation that does not require special IL tolerant enzyme mixtures, or extensive wash 2) eliminates the addition of mineral acids/organic acids and salt accumulation thus making the recycle of IL much easier, 3) allows for 87% glucose and 40% xylose (monomers) yield during saccharification using commercial enzyme mixture; 4) enables direct fermentation of sugars from biomass to 87.7% of the theoretical ethanol yield using wild type fermentation host (*E. coli* or yeast). This study opens avenues for developing more environmentally benign and cost effective processes for sugar product and IL recycling.

4. Experimental

4.1 Materials

Switchgrass (*Panicum virgatum*) was provided by Dr. Daniel Putnam, University of California at Davis. Switchgrass was ground by a Wiley Mill through a 2 mm screen and fractionated by a vibratory sieve system (Endecotts, Ponte Vedra, Fla.). The switchgrass fractions falling between 20 and 40 mesh were collected for use in this study and without drying. The switchgrass contains 29.6% cellulose, 18.4% xylan, 20.0% lignin, 8.1% moisture and 23.9% of other compounds remaining unidentified, on wet basis.[7] Microcrystalline cellulose (MCC, trademark name: Avicel) was purchased from Sigma-Aldrich (St. Louis, Mo.). 1-Ethyl-3-methylimidazolium acetate, abbreviated hereafter as [C2C1Im][OAc], was purchased from BASF (lot no. 08-0010, purity >95%, Basionics™ BC-01, BASF, Florham Park, N.J.). The other imidazolium based ILs were purchased from IoLiTec Ionic Liquids Technologies Inc (Tuscsaloosa, Ala.). Cholinium lysinate ([Ch][Lys]) was synthesized according to the literature,[11] and used after dried under vacuum. The commercial enzyme products cellulase (Cellic® CTec2, Batch # VCN 10001) and hemicellulase (Cellic® HTec2, Batch # VHN00001) were gifts from Novozymes, North America (Franklinton, N.C.).

4.2 Compositional Analysis

Compositional analysis of switchgrass before and after pretreatment was performed using NREL acidolysis protocols (LAP) LAP-002 and LAP-005, which was described in our previous work.[18] Carbohydrate concentrations were determined from the filtrate using an Agilent HPLC 1200 Series equipped with a Bio-Rad Aminex HPX-87H column and a Refractive Index detector. An aqueous solution of $H_2SO_4$ (4 mM) was used as the mobile phase (0.6 mL min$^{-1}$, column temperature 50° C.). The injection volume was 20 μL with a run time of 20 min. Acid insoluble lignin was quantified gravimetrically from the solid after heating overnight at 105° C. (the weight of acid-insoluble lignin+ash) and then at 575° C. for at least 6 h (the weight of ash).

4.3 One-Pot Pretreatment and Saccharification

Switchgrass (100 mg) was mixed with ([Ch][Lys]) at a 10% biomass loading in a 15 mL capped glass pressure tube (Ace Glass) and pretreated in a convection oven at different temperature/time combinations including 90° C. for 5 h, 120° C. for 3 h, and 140° C. for h. Untreated raw switchgrass (30-40 mesh) was used as a control. After pretreatment, the pretreatment slurry was diluted with water to obtain a final IL concentration of 5, 10 or 20 wt %. A CTec2+HTec2 (9:1 v/v) mixture at 10 mg EP per g starting biomass was added to the pretreatment slurry along with citrate buffer (50 mM pH 4.8). Three glass beads were added to each vial to facilitate mixing during enzymatic hydrolysis. Enzymatic hydrolysis using CTec2+HTec2 mixture was conducted at 50° C., with constant agitation on an Enviro Genie SI-1200 rotator platform (Scientific Industries, Inc., Bohemia, N.Y.). For comparison, the whole pretreatment slurry was washed 6 times with hot water to remove residual ILs and soluble sugars. Washed IL-pretreated solids were dried by lyophilization, weighed and resuspended with water or buffer solution before adding the CTec2+HTec2 enzyme mixture.

In another set of pretreatment, switchgrass (100 mg, dry weight) was mixed with 5, 10, and 20% [Ch][Lys]-water solutions at a 10% biomass loading in a 15 ml capped glass pressure tube and pretreated at 140° C. for 1 h. After pretreatment, CTec2+HTec2 (9:1 v/v) mixture was directly added to the pretreatment slurry at 10 mg EP per g starting biomass for saccharification at the same conditions as stated above. In addition, microcrystalline cellulose (MCC) was hydrolyzed by 30 mg/g starting biomass for CTec2+HTec2, spiked with 0-30% IL.

4.4 $CO_2$-Based pH Adjustment

All the $CO_2$ absorption experiments were carried out at room temperature in a 25 mL stainless steel Parr reactor (Parr instrument Co., USA) equipped with a magnetic stirrer plate and $CO_2$ cylinder (>99.9% $CO_2$ purity). In a typical procedure, 10 mL a certain concentration of [Ch][Lys] aqueous system was added into the Parr. After being sealed, the Parr was stirred at room temperature, and the absorption pressure was held constant by a backpressure valve. After the absorption was completed, the Parr was cooled to ambient temperature, and the remaining $CO_2$ was removed slowly. Then, the corresponding pH value of the mixture was analyzed by Orion™ 3-Star Benchtop pH Meter. To elucidate the interaction between $CO_2$ with side amine and terminal amine groups of [Ch][Lys] in $H_2O$, we conducted $^{13}C$ nuclear magnetic resonance (NMR) analysis of [Ch][Lys] before and after $CO_2$ absorption. Furthermore, two-dimensional (2D)$^{13}C$-$^1H$ heteronuclear single quantum coherence (HSQC) and heteronuclear multiple bond correlation (HMBC) nuclear magnetic resonance (NMR) analysis were also carried out on [Ch][Lys] before and after $CO_2$ absorption.

4.5 Simultaneous Saccharification and Fermentation

Yeast (*Saccharomyces cerevisiae*) strain BY4741 (ATCC 4040002) was propagated in liquid YPD media for 24 h. The cells were recovered by centrifugation at 3220 rcf for 5 min and washed three times by 0.2% sterile peptone solution. Switchgrass (600 mg) was mixed with 5.4 ml of 10% [Ch][Lys]-water solutions at a 10% biomass loading in a 15 mL capped glass pressure tube and pretreated at 140° C. for 1 h. After pretreatment, the pretreated slurry was diluted with 6 ml water and CTec2+HTec2 (9:1 v/v) mixture was then added at 10 mg EP per g starting biomass. The mixture was carbonated under 1 MPa $CO_2$ pressure and incubated at 50° C. for 18 h for saccharification and then cooled down to 37° C. for yeast inoculation to a concentration of 5 g/L yeast cells (based on dry weight). After 72 h of simultaneous saccharification and fermentation (SSF), the fermentation broth was chilled on ice and centrifuged to separate the solid and liquid. The liquid was analyzed for cellobiose, glucose, xylose, acetic acid and ethanol on HPLC as described in section 4.2. The solids were washed thoroughly with water and lyophilized for composition analysis and lignin characterization.

4.6 Theoretical Computation

All of the calculations were performed with the Gaussian 09 software package. The geometries of all of the [Ch][Lys] IL, $CO_2$ mediated IL complexes, and complexes with $H_2O$ involved in the bicarbonate formation were fully optimized at the M06-2X/6-311++G(d, p) level of theory. Harmonic frequency calculations were performed at the equilibrium geometries to confirm first-order saddle points and local minima on the potential energy surfaces. The stable structures were verified by analyzing the corresponding geometries (optimized structures in different conformations) obtained from our calculations and interaction energies (IEs) were corrected for basis set superposition error (BSSE). In the present study, acidity values were calculated using the density functional theory (DFT) based global reactivity descriptors,[27] such as chemical hardness and chemical potential[29] of the IL-$H_2O$—$CO_2$ complexes. Natural bond orbital analyses at the M06-2X/6-311++G(d, p) level were performed to determine the atomic charge populations and local nucleophilicity values[30] obtained for nitrogen atoms of lysinate ion involved in the complexes.

REFERENCES CITED

1. Schubert C. Can biofuels finally take center stage? *Nature Biotechnology* 2006, 24(7): 777-784.
2. Gelfand I, Sahajpal R, Zhang X, Izaurralde R C, Gross K L, Robertson G P. Sustainable bioenergy production from marginal lands in the US Midwest. *Nature* 2013, 493 (7433): 514-517.
3. Wang H, Gurau G, Rogers R D. Ionic liquid processing of cellulose. *Chemical Society Reviews* 2012, 41(4): 1519-1537.
4. Shi J, Thompson V S, Yancey N A, Stavila V, Simmons B A, Singh S. Impact of mixed feedstocks and feedstock densification on ionic liquid pretreatment efficiency. Biofuels 2013, 4(1): 63-72.
5. Li C L, Tanjore D, He W, Wong J, Gardner J L, Sale K L, et al. Scale-up and evaluation of high solid ionic liquid pretreatment and enzymatic hydrolysis of switchgrass. *Biotechnology for Biofuels* 2013, 6.
6. da Silva A S A, Teixeira R S S, Endo T, Bon E P S, Lee S-H. Continuous pretreatment of sugarcane bagasse at high loading in an ionic liquid using a twin-screw extruder. *Green Chemistry* 2013, 15(7): 1991-2001.

7. Shi J, Gladden J M, Sathitsuksanoh N, Kambam P, Sandoval L, Mitra D, et al. One-pot ionic liquid pretreatment and saccharification of switchgrass. *Green Chemistry* 2013, 15(9): 2579-2589.
8. Ruegg T L, Kim E-M, Simmons B A, Keasling J D, Singer S W, Soon Lee T, et al. An auto-inducible mechanism for ionic liquid resistance in microbial biofuel production. *Nat Commun* 2014, 5.
9. Ninomiya K, Yamauchi T, Kobayashi M, Ogino C, Shimizu N, Takahashi K. Cholinium carboxylate ionic liquids for pretreatment of lignocellulosic materials to enhance subsequent enzymatic saccharification. *Biochemical Engineering Journal* 2013, 71(0): 25-29.
10. Ohira K, Abe Y, Kawatsura M, Suzuki K, Mizuno M, Amano Y, et al. Design of Cellulose Dissolving Ionic Liquids Inspired by Nature. *ChemSusChem* 2012, 5(2): 388-391.
11. Liu Q-P, Hou X-D, Li N, Zong M-H. Ionic liquids from renewable biomaterials: synthesis, characterization and application in the pretreatment of biomass. *Green Chemistry* 2012, 14(2): 304-307.
12. Hou X-D, Liu Q-P, Smith T J, Li N, Zong M-H. Evaluation of Toxicity and Biodegradability of Cholinium Amino Acids Ionic Liquids. *PLoS ONE* 2013, 8(3): e59145.
13. Tome L C, Patinha D J S, Ferreira R, Garcia H, Silva Pereira C, Freire C S R, et al. Cholinium-based Supported Ionic Liquid Membranes: A Sustainable Route for Carbon Dioxide Separation. *ChemSusChem* 2014, 7(1): 110-113.
14. Fukaya Y, Iizuka Y, Sekikawa K, Ohno H. Bio ionic liquids: room temperature ionic liquids composed wholly of biomaterials. *Green Chemistry* 2007, 9(11): 1155-1157.
15. Plechkova N V, Seddon K R. Applications of ionic liquids in the chemical industry. *Chemical Society Reviews* 2008, 37(1): 123-150.
16. Petkovic M, Ferguson J, Bohn A, Trindade J, Martins I, Carvalho M B, et al. Exploring fungal activity in the presence of ionic liquids. *Green Chemistry* 2009, 11(6): 889-894.
17. Boethling R S, Sommer E, DiFiore D. Designing Small Molecules for Biodegradability. *Chemical Reviews* 2007, 107(6): 2207-2227.
18. Sun N, Parthasarathi R, Socha A M, Shi J, Zhang S, Stavila V, et al. Understanding pretreatment efficacy of four cholinium and imidazolium ionic liquids by chemistry and computation. *Green Chemistry* 2014, 16(5): 2546-2557.
19. Tome L C, Patinha D J S, Ferreira R, Garcia H, Pereira C S, Freire C S R, et al. Cholinium-based Supported Ionic Liquid Membranes: A Sustainable Route for Carbon Dioxide Separation. *Chemsuschem* 2014, 7(1): 110-113.
20. Yang Z-Z, He L-N, Zhao Y-N, Li B, Yu B. CO2 capture and activation by superbase/polyethylene glycol and its subsequent conversion. *Energy & Environmental Science* 2011, 4(10): 3971-3975.
21. Petkovic M, Seddon K R, Rebelo L P N, Silva Pereira C. Ionic liquids: a pathway to environmental acceptability. *Chemical Society Reviews* 2011, 40(3): 1383-1403.
22. Frederix M, Hütter K, Leu J, Batth T S, Turner W J, Rüegg T L, et al. Development of a Native *Escherichia coli* Induction System for Ionic Liquid Tolerance. *PLoS ONE* 2014, 9(7): e101115.
23. Ober C A, Gupta R B. pH Control of Ionic Liquids with Carbon Dioxide and Water: 1-Ethyl-3-methylimidazolium Acetate. *Industrial & Engineering Chemistry Research* 2012, 51(6): 2524-2530.
24. Pera-Titus M. Porous Inorganic Membranes for CO2 Capture: Present and Prospects. *Chemical Reviews* 2013, 114(2): 1413-1492.
25. Jessop P G, Subramaniam B. Gas-Expanded Liquids. *Chemical Reviews* 2007, 107(6): 2666-2694.
26. Barber P S, Griggs C S, Gurau G, Liu Z, Li S, Li Z, et al. Coagulation of Chitin and Cellulose from 1-Ethyl-3-methylimidazolium Acetate Ionic-Liquid Solutions Using Carbon Dioxide. *Angewandte Chemie International Edition* 2013, 52(47): 12350-12353.
27. Shi J, Balamurugan K, Parthasarathi R, Sathitsuksanoh N, Zhang S, Stavila V, et al. Understanding the role of water during ionic liquid pretreatment of lignocellulose: co-solvent or anti-solvent? *Green Chemistry* 2014, 16(8): 3830-3840.
28. Socha A M, Parthasarathi R, Shi J, Pattathil S, Whyte D, Bergeron M, et al. Efficient biomass pretreatment using ionic liquids derived from lignin and hemicellulose. *Proceedings of the National Academy of Sciences* 2014, 11 (35): E3587-E3595.
29. Parr R G, Yang W. *Density-functional theory of atoms and molecules*, vol. 16. Oxford university press, 1989.
30. Parthasarathi R, Padmanabhan J, Elango M, Subramanian V, Chattaraj P. Intermolecular reactivity through the generalized philicity concept. *Chemical physics letters* 2004, 394(4): 225-230.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A method of hydrolyzing a biomass comprising:
(a) (i) contacting a biomass comprising a polysaccharide and an ionic liquid to form a pre-treated biomass solution, or (ii) providing the pre-treated biomass solution comprising the biomass and the ionic liquid,
wherein the ionic liquid comprises cholinium lysinate ([Ch][Lys]), and
wherein the pH of the pre-treated biomass solution ranges from 12 to 14;
(b) contacting the pre-treated biomass solution and gaseous carbon dioxide such that the pH of the pre-treated biomass solution ranges from 4.5 to 7.5, wherein the gaseous carbon dioxide has a pressure ranging from 0.1 MPa to 2 MPa, thereby forming a pH-adjusted pre-treated biomass solution,
(c) introducing directly to the pH-adjusted pre-treated biomass solution (i) a cellulase, a hemicellulase, or a mixture of a cellulase and a hemicellulase, such that the polysaccharide is at least partially broken down, thereby forming a hydrolyzed biomass;
(d) optionally separating a solid portion and a liquid portion of the hydrolyzed biomass, and
(e) optionally recovering the ionic liquid from the liquid portion of the hydrolyzed biomass.
2. The method of claim 1, wherein step (a) comprises heating the biomass and the ionic liquid at a temperature ranging from room temperature to 150° C.

3. The method of claim 1, wherein step (c) further comprises combining the hydrolyzed biomass with a microorganism for fermentation at a temperature ranging from room temperature to 37° C.

4. The method of claim 1, wherein the biomass is a biomass derived from a hardwood feedstock, a softwood feedstock, a grass feedstock, or an agricultural waste feedstock, or a mixture thereof.

5. The method of claim 1, wherein the biomass comprises algal biomass, municipal solid waste, food processing waste, or a mixture thereof.

6. The method of claim 1, wherein the gaseous carbon dioxide has a pressure of 1 MPa.

7. The method of claim 1, wherein the polysaccharide is a cellulose, hemicellulose, lignin-hemicellulose, lignin, chitin, agarose, or a mixture thereof.

8. The method of claim 1, wherein the cellulase, the hemicellulase, or the mixture of the cellulase and the hemicellulase has an optimal activity at a pH from pH 4.5 to pH 8.0.

9. The method of claim 3, wherein the microorganism is a yeast or a prokaryote.

10. The method of claim 9, wherein the prokaryote is a-*Zymomonas* species, *Streptomyces* species, *Clostridium* species, *Klebsiella* species, *Ralstonia* species, *Bacillus* species, *Pseudomonas* species, or *Escherichia* species.

11. The method of claim 1, wherein the separating step (d) comprises centrifuging the hydrolyzed biomass.

12. The method of claim 1, wherein the contacting step (a) is repeated with a fresh biomass and the ionic liquid used comprises in part at least some of the ionic liquid recovered from the recovering step (e).

13. The method of claim 12, wherein the method steps are repeated for a plurality of times wherein for each contacting step (a), except for the first time contacting step (a) takes place, the ionic liquid used comprises in part at least some of the ionic liquid recovered from the recovering step (e).

14. The method of claim 1, wherein the separating step (d) occurs immediately subsequent to the recovering step (e).

15. The method of claim 1, wherein the method results in glucan, xylan, lignin, or a mixture thereof in the solid portion of the hydrolyzed biomass.

16. The method of claim 1, wherein the method results in a hexose or oligomer thereof, a pentose or oligomer thereof, ethanol, or a mixture thereof in the liquid portion of the hydrolyzed biomass.

17. The method of claim 1, wherein the method further comprises a releasing step comprising releasing carbon dioxide by either elevating the temperature or introducing nitrogen gas, or both.

* * * * *